(12) United States Patent
Steere, III et al.

(10) Patent No.: US 7,240,538 B1
(45) Date of Patent: Jul. 10, 2007

(54) HYDRO TEST APPARATUS AND METHOD FOR AMMUNITION

(75) Inventors: Robert E. Steere, III, Boonton, NJ (US); Michael Spielzinger, Staten Island, NY (US); Vincent Gonsalves, Nazareth, PA (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 165 days.

(21) Appl. No.: 11/161,774

(22) Filed: Aug. 16, 2005

Related U.S. Application Data

(60) Provisional application No. 60/522,167, filed on Aug. 24, 2004.

(51) Int. Cl.
*G01M 3/04* (2006.01)
*G01L 5/14* (2006.01)

(52) U.S. Cl. .......................................... 73/49.5; 73/167
(58) Field of Classification Search ................. 73/49.5, 73/49.6, 167
See application file for complete search history.

(56) References Cited

U.S. PATENT DOCUMENTS

| | | | | |
|---|---|---|---|---|
| 3,616,685 A * | 11/1971 | Strom | ........................... | 73/84 |
| 3,760,632 A * | 9/1973 | Illyes et al. | ................... | 73/49.6 |
| 4,127,026 A * | 11/1978 | Battafarano | .................. | 73/49.5 |
| 4,192,177 A * | 3/1980 | Crickard et al. | ............. | 73/49.5 |
| 4,211,107 A * | 7/1980 | Sleeter et al. | ................ | 73/49.6 |
| 4,413,501 A * | 11/1983 | Schrock | ....................... | 73/49.6 |
| 4,416,147 A * | 11/1983 | Hasha | ......................... | 73/49.6 |
| 4,502,323 A * | 3/1985 | Watase et al. | ............... | 73/49.6 |
| 4,764,332 A * | 8/1988 | Guina | ......................... | 376/203 |
| 4,838,075 A * | 6/1989 | Friedrich et al. | ............ | 73/49.8 |
| 6,619,104 B1 * | 9/2003 | Yeh | ............................. | 73/49.6 |

\* cited by examiner

*Primary Examiner*—Hezron Williams
*Assistant Examiner*—John Fitzgerald
(74) *Attorney, Agent, or Firm*—John F. Moran

(57) ABSTRACT

An apparatus for hydrotesting a hollow component includes a generally cylindrical main body having a bore therethrough that defines first and second open ends, the bore including a central axis; first and second end plates fixed to the main body for closing the first and second open ends, the first end plate including a vent port and a pressure port that open into the bore radially distal from the central axis, the second end plate including a vent port and a pressure port; an alignment disc disposed in the bore and fixed atop the second end plate, the alignment disc including a vent port and a pressure port that open into the bore radially proximal the central axis, the vent port and the pressure port of the alignment disc being in fluid communication with the vent port and the pressure port, respectively, of the second end plate; and a movable sealing cap disposed in an opening in the first plate and movable along the central axis of the bore.

21 Claims, 6 Drawing Sheets

HYDRO TEST APPARATUS AND METHOD FOR AMMUNITION

CROSS-REFERENCE TO RELATED APPLICATIONS

This application claims the benefit under 35 USC 119(e) of U.S. provisional patent application 60/522,167 filed on Aug. 24, 2004, which application is hereby incorporated by reference.

STATEMENT OF GOVERNMENT INTEREST

The inventions described herein may be manufactured, used and licensed by or for the U.S. Government for U.S. Government purposes.

BACKGROUND OF THE INVENTION

The invention relates in general to apparatus and methods for testing ammunition, and in particular to apparatus and methods for testing the structural integrity of a mortar fragmentation body.

During launch, high pressures are applied externally to the outer surface of a projectile. These high external pressures create inward forces that can collapse the projectile. Internal testing has been the traditional method of testing ammunition components. An internal hydrotest is much easier to perform, however, internal testing typically requires a large compromise on the load being applied. The internal test load produces stresses that are very different from the stresses produced during an actual launch.

The present invention provides apparatus and method for externally testing ammunition components. The invention can be used in a destructive mode (at higher pressure) to validate computer modeling. Or, the invention can be used in the normal non-destructive mode at launch pressure that is intended to be used 100% during production to detect and screen out critical defects. The invention can also be used to apply hydrostatic pressure internally.

SUMMARY OF THE INVENTION

One aspect of the invention is an apparatus comprising a generally cylindrical main body having a bore therethrough that defines first and second open ends, the bore including a central axis; first and second end plates fixed to the main body for closing the first and second open ends, the first end plate including a vent port and a pressure port that open into the bore radially distal from the central axis, the second end plate including a vent port and a pressure port; an alignment disc disposed in the bore and fixed atop the second end plate, the alignment disc including a vent port and a pressure port that open into the bore radially proximal the central axis, the vent port and the pressure port of the alignment disc being in fluid communication with the vent port and the pressure port, respectively, of the second end plate; and a movable sealing cap disposed in an opening in the first plate and movable along the central axis of the bore.

Another aspect of the invention is an apparatus for hydrotesting a hollow component having an open base and an open top comprising a generally cylindrical main body having a bore therethrough that defines first and second open ends, the bore including a central axis, the hollow component being disposed in the bore in the main body; first and second end plates fixed to the main body for closing the first and second open ends, the first end plate including a vent port and a pressure port that open into the bore radially outward from the open top of the hollow component, the second end plate including a vent port and a pressure port; an alignment disc disposed in the bore and fixed atop the second end plate, the alignment disc including a vent port and a pressure port that open into the bore radially inside the open base of the hollow component, the vent port and the pressure port of the alignment disc being in fluid communication with the vent port and the pressure port, respectively, of the second end plate, the open base of the hollow component being inserted over the alignment disc; and a movable sealing cap disposed in an opening in the first plate and movable along the central axis of the bore, the movable sealing cap closing the open top of the hollow component.

A further aspect of the invention is a method of testing a hollow component having open ends, comprising placing the hollow component in a test apparatus; sealing the open ends of the hollow component; and increasing pressure in a space between the hollow component and the test apparatus to thereby apply pressure to the external surface of the hollow component.

The invention will be better understood, and further objects, features, and advantages thereof will become more apparent from the following description of the preferred embodiments, taken in conjunction with the accompanying drawings.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

Figures 1A, 1B:
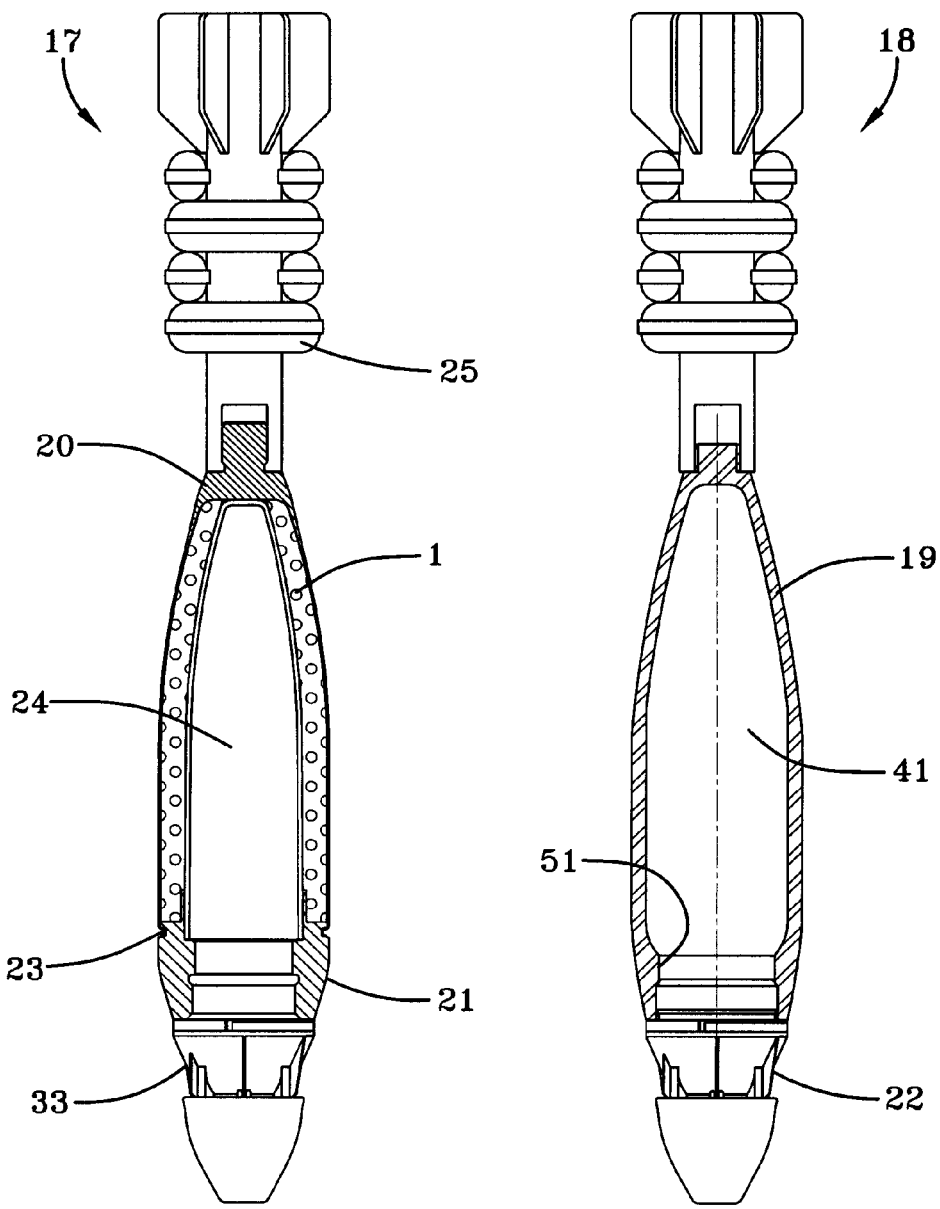
FIG. 1A is a sectional view of one embodiment of a mortar round.
FIG. 1B is a sectional view of another embodiment of a mortar round.

FIG. 1A is a sectional view of one embodiment of a mortar round 17. FIG. 1B is a sectional view of an embodiment of a traditional mortar round 18. Referring to FIG. 1A, the fragmentation body 1 plays a critical role during the launch of a mortar 17. Fragmentation body 1 provides the structural strength to survive launching pressures created by propelling charges 25. Failure of the fragmentation body 1 to survive the launch results in premature detonation of the explosive charge 24, or the mortar 17 falling short of its intended target. Both scenarios are critical failures that expose friendly troops to the lethality of the mortar.

Comparing the two mortars 17, 18 shown in FIGS. 1A and 1B, the traditional mortar assembly 18 comprises fewer parts. In mortar 17, the traditional steel body 19 of mortar 18 has been replaced by the combination of a thinned wall case 20, a fragmentation body 1 and an adapter 21 (FIG. 1A). The combination of the thinned wall case 20, fragmentation body 1 and adapter 21 is fixed together with, for example, glue and a continuous crimp 23 of the case 20 to the adapter 21. The fuze 22 of the traditional mortar 18 is fixed to the steel body 19 via thread 51, whereas the fuze 33 of mortar 17 is threaded into adapter 21.

The steel body 19 of the traditional mortar 18 is the critical component providing structural integrity to survive launch. Therefore, stringent inspections exist in current production lines to prevent defective parts from reaching the field. One such inspection is the internal hydro (pressure) test. The inside cavity 41 of the steel body 19 is pressurized to a value below the yield strength of steel, but high enough to break the steel body 19 if it contains defects such as critical cracks or internal fractures. The internal hydro test method neither simulates the external pressures that mortar ammunition experiences during launch, nor does it test the strength of the body everywhere at the desired stress level (80% of yield strength), due to variations in the geometry of the component. However, computer modeling and simulation has provided a high degree of confidence that if the steel body 19 survives the internal pressure test, it will have sufficient structural soundness to survive external launch pressures.

Figure 2A:
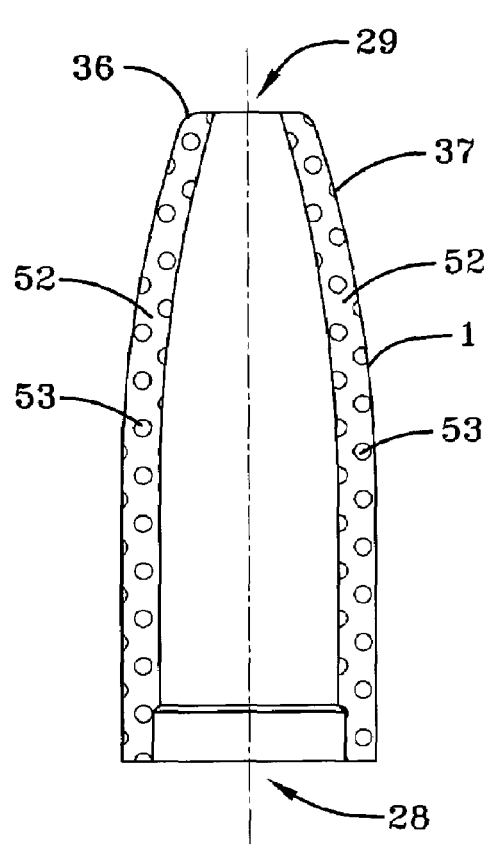
FIG. 2A shows the fragmentation body of the mortar round of FIG. 1A.
Figure 2B:
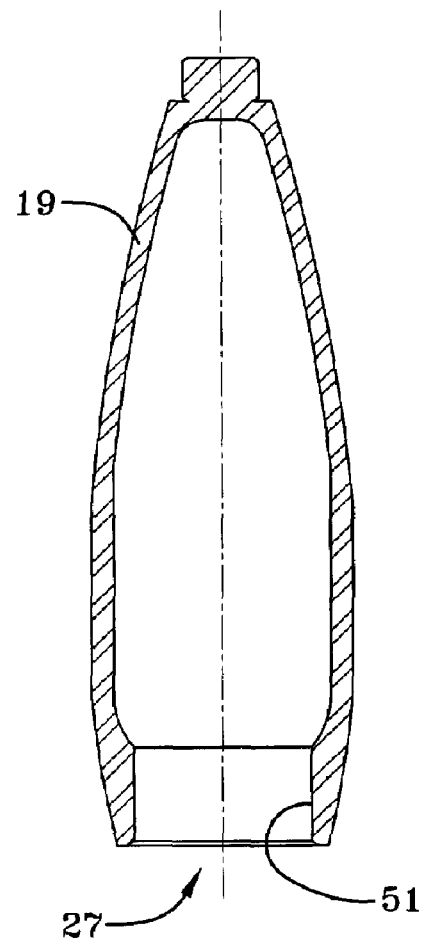
FIG. 2B shows the body of the mortar round of FIG. 1B.

FIG. 2A shows the fragmentation body 1 of the mortar round 17 of FIG. 1A. FIG. 2B shows the body 19 of the mortar round 18 of FIG. 1B. The fragmentation body 1 of mortar 17 is considered a critical structural component. This classification requires validated computer modeling analysis and a non-destructive inspection method to detect structural defects during production. The fragmentation body 1 is made of a non-uniform material matrix comprising a moldable material 52 with randomly dispersed metal balls 53 throughout. The strength of the fragmentation body 1 varies, depending on the random locations of the metal balls 53 and anomalies from the molding process, such as pits, voids, and material consistency. The shape of the fragmentation body 1 differs from the traditional steel mortar body 19 in that both ends 28 and 29 of the fragmentation body 1 are open, while the traditional steel mortar body 19 has only one open end 27, comprising a thread 51.

Figure 3:
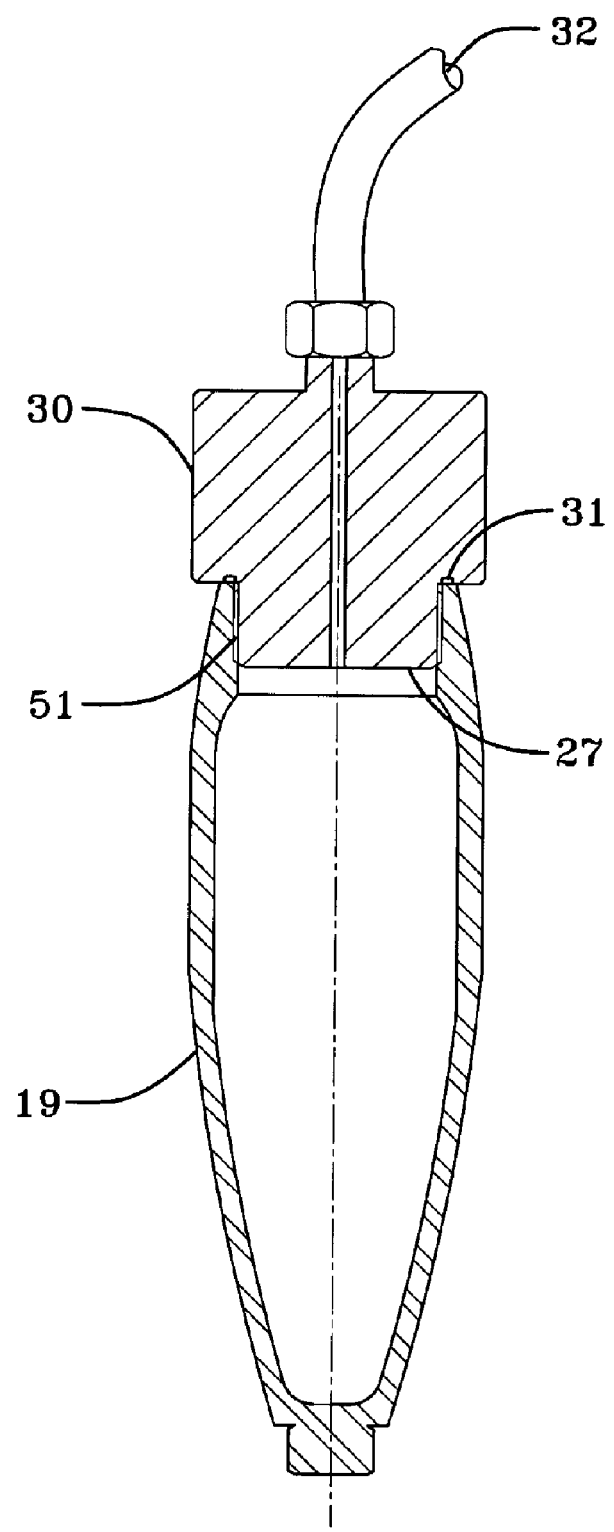
FIG. 3 shows a hydro test apparatus for the body of FIG. 2B.

FIG. 3 shows a hydro test apparatus for the body 19 of FIG. 2B. The structural integrity of the traditional steel mortar body 19 is inspected using an internal pressure. The open end 27 of the steel body 19 is sealed by O-ring 31 after threading the steel body 19 onto the adapter 30 via thread 51. Pressure is then introduced inside the steel body 19 through supply line 32. The supply line pressure is regulated to approach but not exceed the yield strength of the steel body 19.

In the present invention, an external pressure is applied to the fragmentation body 1, rather than the traditional approach of using an internal pressure. The external pressure method is more appropriate for the fragmentation body 1, and more closely simulates the compressive stresses experienced during a mortar launch. Applying an internal pressure to the fragmentation body 1 creates a condition of tension in the body 1. This tension in the body 1 tends to propagate cracks and fractures and break small cross-sectional areas created by the metal balls 53 and their low adhesion to the moldable material 52. The internal pressure test can lead to the rejection of useable bodies 1, because tests have shown that small cracks and fractures in the fragmentation body 1 do survive mortar launch conditions.

Traditional steel mortar bodies 19, however, must be free of cracks and fractures because they can cause a failure during launch. This is because the traditional mortar body 19 additionally functions as the primary protective barrier, preventing hot gases created during launch from reaching and prematurely detonating the mortar's high explosive material in cavity 41. The fragmentation body 1, however, does not act as the primary protective barrier to the hot launch gases and therefore can function with cracks or fractures. In the mortar 17, the case 20 covers the outer surface of the fragmentation body 1 and acts as the primary barrier to the hot launch gases.

Figure 4:
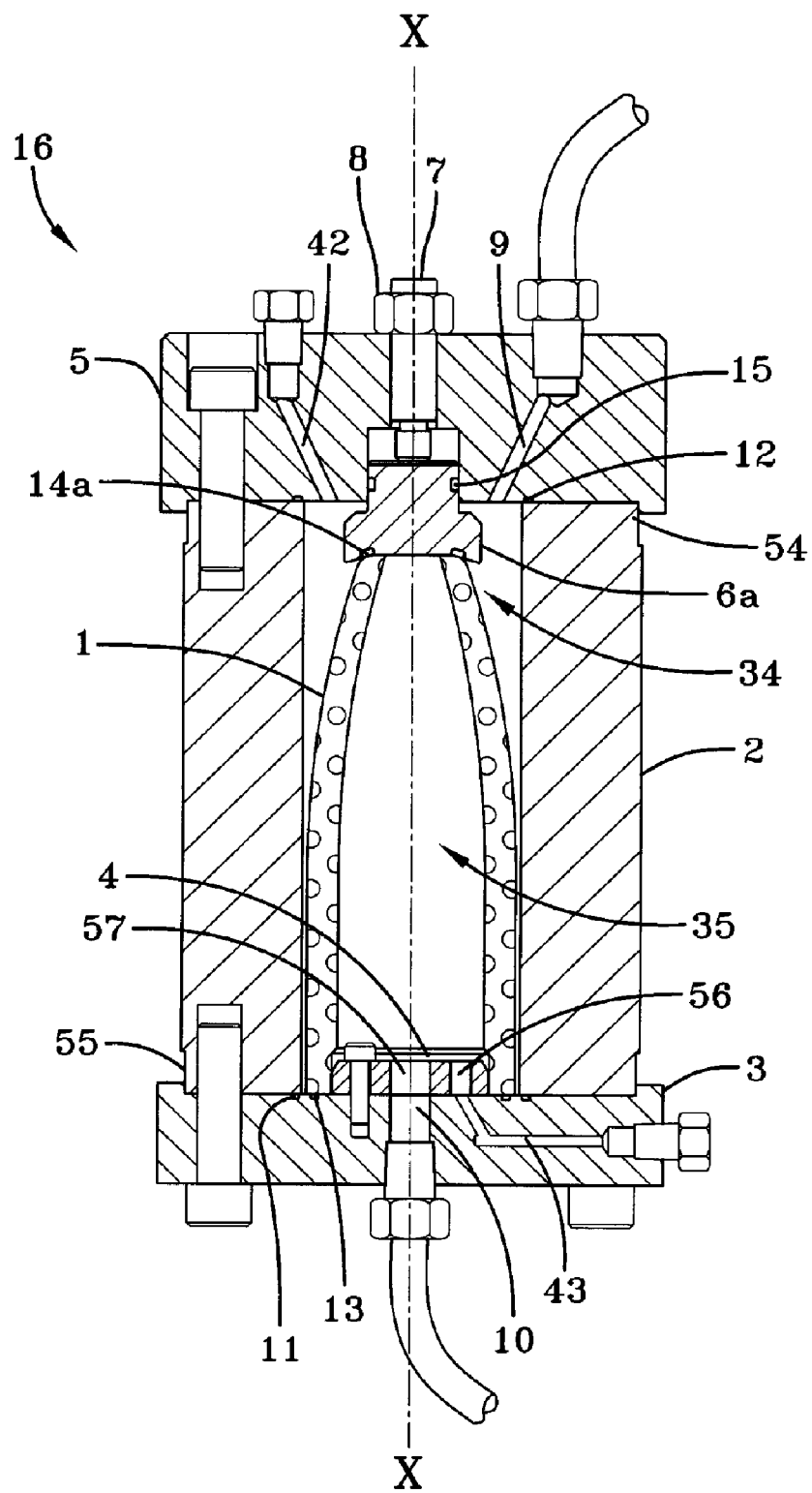
FIG. 4 is a sectional view of one embodiment of a hydro test apparatus according to the invention.

FIG. 4 is a sectional view of one embodiment of a hydro test apparatus 16 according to the invention. The apparatus 16 comprises a generally cylindrical main body 2 having a bore 34 therethrough that defines first and second open ends. The bore 34 includes a central axis X. First and second end plates 5, 3 are fixed to the main body 2 for closing the first and second open ends. The first and second open ends of the main body 2 include pilot diameters 54, 55 that mate with recesses formed in the first and second end plates 5, 3, respectively.

The first end plate 5 includes an air escape or vent port 42 and a pressure port 9 both of which open into the bore 34 radially distal from the central axis X. That is, the ports 42, 9 open into the bore 34 external to the fragmentation body 1. In general, the fragmentation body 1 may be any hollow component open at both ends. The second end plate 3 includes an air escape or vent port 43 and a pressure port 10. An alignment disc 4 is fixed to the second end plate 3. The alignment disc 4 includes a vent port 56 and a pressure port 57 that open into the bore 34 radially proximal the central axis X. That is, the ports 56, 57 open into the interior 35 of the fragmentation body 1 when the body 1 is mounted in the apparatus 16. The vent port 56 and pressure port 57 are in fluid communication with the vent port 43 and pressure port 10, respectively, of the second end plate 3. A moveable sealing cap 6a is located in an opening in the first end plate 5 and is movable along the central axis X.

The fragmentation body 1 is placed with open end 28 over the alignment disk 4. The sealing cap 6a is moved inward to clamp the fragmentation body 1 against the second plate 3. Movement of the sealing cap 6a is performed, for example, via a swivel foot socket set screw 7 which is locked into final position using locking nut 8. Seals, for example, O-rings 11, 12, are disposed between the main body 2 and the end plates 5, 3 to seal the cavity 34. A seal, for example, O-ring 13, is disposed between the open base of the fragmentation body 1 and the second plate 3. Another seal, for example, O-ring 14a is disposed between the open top of the fragmentation body 1 and the sealing cap 6a. The sealing cap 6a is dynamically sealed by O-ring 15 disposed between the sealing cap 6a and the end plate 5.

The novel method of the invention uses external pressure to test the fragmentation body 1. That is, the space between the main body 2 and the fragmentation body 1 is pressurized. However, the apparatus 16 may be used for both external and internal pressure tests. There are two interchangeable sealing caps 6a and 6b (FIGS. 6 and 5) that seal against the upper face of the fragmentation body 1. If external pressure is desired, then sealing cap 6a is used. If internal pressure is desired, then sealing cap 6b is used.

Figure 6:
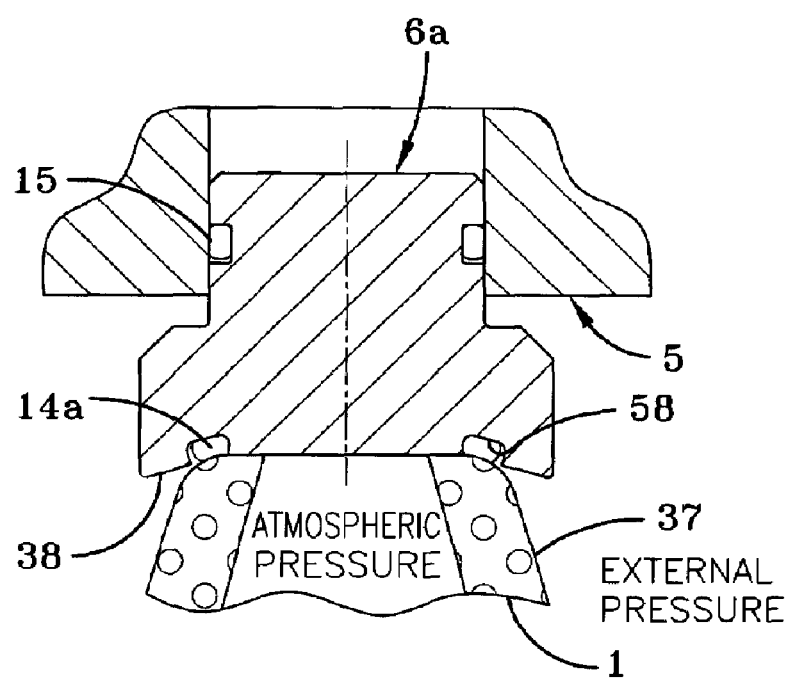
FIG. 6 shows a sealing cap used for external pressure testing.

FIG. 6 shows the sealing cap 6a used for external pressure testing. The external pressure sealing cap 6a seals against the open top of the fragmentation body 1. A groove 58 is formed in the bottom surface of the sealing cap 6a and O-ring 14a is disposed in groove 58. Preferably, the O-ring seal 14a is located at the outermost diameter of the open top of the fragmentation body 1. This location minimizes the axial stress between the cap 6a and the open top of fragmentation body 1 by maximizing the contact area. This location of the O-ring seal 14a also avoids having to seal completely against the blend radius 36, which is subject to process variation. Only the upper face of the fragmentation body 1 contacts the cap 6a. If cap 6a were to contact the blend radius 36 or outer profile 37 of the fragmentation body 1, the fragmentation body 1 could potentially be damaged.

Figure 7:
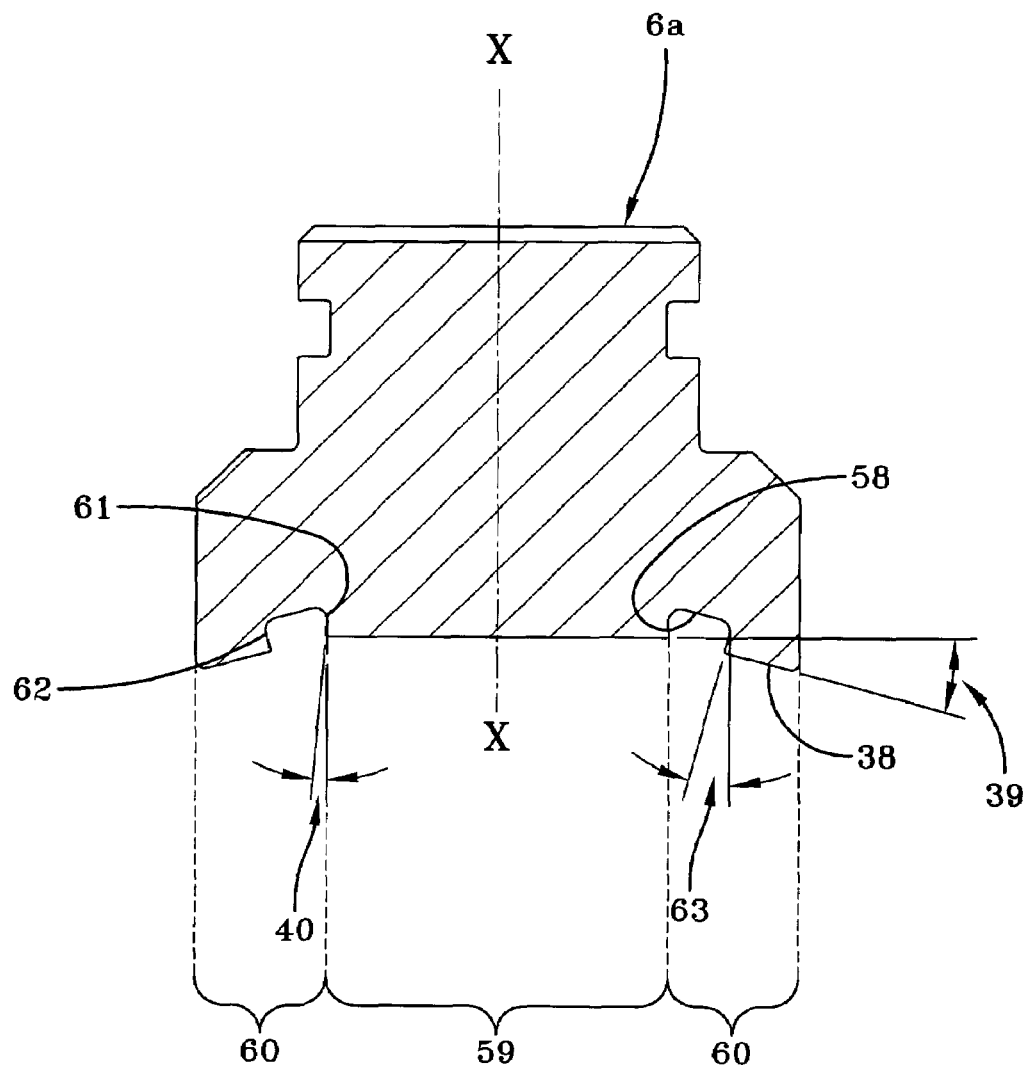
FIG. 7 is an enlarged view of the sealing cap of FIG. 6.

FIG. 7 is an enlarged view of the sealing cap 6a of FIG. 6. The bottom surface of the sealing cap 6a includes an inner portion 59 that is substantially perpendicular to the central axis X of the main body 2 and an outer portion 60 that forms an angle 39 with respect to the inner portion 59. The outer portion 60 includes the groove 58. Angle 39 helps contain O-ring 14a in the region of the blend radius 36. Without angle 39, the O-ring 14a would be not be adequately compressed to seal the external pressure build up. In a preferred embodiment, angle 39 is about twenty-five degrees. Groove 58 includes inner side wall 61 and outer side wall 62. The inner side wall 61 is angled inwardly (angle 40) with respect to central axis X and the outer side wall is angled outwardly (angle 63) with respect to the central axis X. Exemplary values for angles 40 and 63 are about five degrees and about fifteen degrees, respectively. Angles 40 and 63 help retain O-ring 14a in groove 58 when the fragmentation body 1 is not in contact with seal cap 6a.

Referring to FIG. 6, the two O-ring seals 14a and 15 are preferably about the same diameter. The similar diameters of seals 14a and 15 minimizes the axial force of the sealing cap 6a towards or away from the fragmentation body 1. Minimizing the axial force towards the fragmentation body 1 reduces damage from the sealing cap contacting the fragmentation body 1, and minimizing the axial force in the opposite direction reduces the force on the swivel foot socket setscrew 7.

Figure 5:
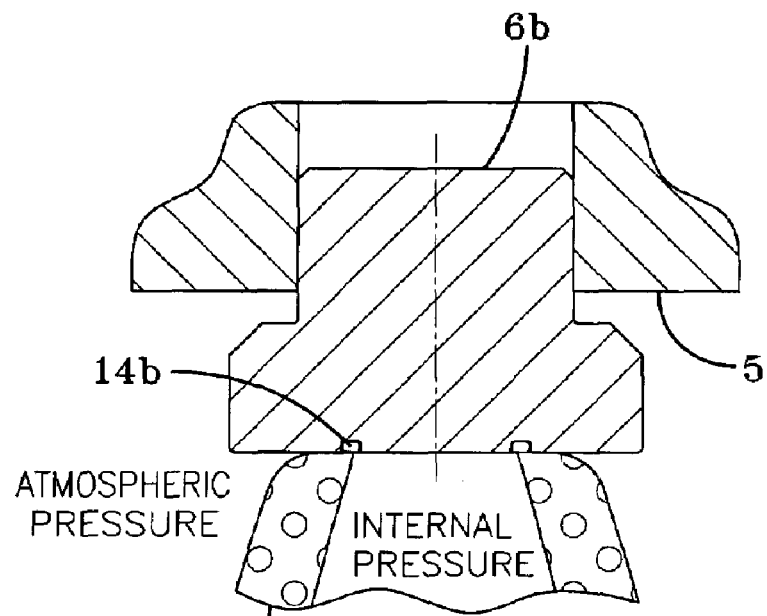
FIG. 5 shows a sealing cap used for internal pressure testing.

FIG. 5 shows a sealing cap 6b used for internal pressure testing. The internal pressure sealing cap 6b supports pressure internal to the fragmentation body 1. O-ring 14b is used to provide a static seal between seal cap 6b and the upper face of the fragmentation body 1. No dynamic seal is required between seal cap 6b and first end plate 5. O-rings 11, 12, 13, 14a, and 14b (FIGS. 4 and 5) are designed for minimal wear by employing a static face seal. O-ring 15 (FIG. 6) is a dynamic seal, allowing movement of the sealing cap 6a (external pressure mode) in order to accommodate piece-to-piece length variations of the fragmentation body 1.

To operate the apparatus 16 in the external pressure mode, the fragmentation body 1 is placed inside main body 2 over alignment disk 4. The first end plate 5, configured with seal cap 6a, is then installed. Next, the swivel foot socket set screw 7 is used to lower the seal cap 6a into contact with the upper face of the fragmentation body 1. Once the seal cap 6a is in position, the swivel foot socket set screw 7 is locked into final position using locking nut 8. Fluid enters into the chamber cavity 34 via port 9. As the fluid fills the cavity 34, air escapes through the bleed-off port 42. Once the air is bled off, the bleed-off port 42 is closed. Pressure is then built up in the chamber cavity 34 via port 9. The pressure build-up is on the outside of the fragmentation body 1 while the open volume 35 inside the fragmentation body 1 remains at atmospheric pressure.

To operate the apparatus 16 in the internal pressure mode, the first end plate 5 is configured with sealing cap 6b, and the fragmentation body 1 is loaded into the fixture using the same procedure as described above for the external pressure mode. Fluid is then introduced into the open volume 35 inside of the fragmentation body 1 via port 10. As the fluid fills the open volume 35, the displaced air escapes through bleed-off port 43. Once the air has been evacuated and the bleed-off port 43 closed, the pressure builds-up is on the inside of the fragmentation body 1 while the chamber cavity 34 remains at atmospheric pressure.

While the invention has been described with reference to certain preferred embodiments, numerous changes, alterations and modifications to the described embodiments are possible without departing from the spirit and scope of the invention as defined in the appended claims, and equivalents thereof.

What is claimed is:

1. An apparatus, comprising:
   a generally cylindrical main body having a bore therethrough that defines first and second open ends, the bore including a central axis;
   first and second end plates fixed to the main body for closing the first and second open ends, the first end plate including a vent port and a pressure port that open into the bore radially distal from the central axis, the second end plate including a vent port and a pressure port;
   an alignment disc disposed in the bore and fixed atop the second end plate, the alignment disc including a vent port and a pressure port that open into the bore radially proximal the central axis, the vent port and the pressure port of the alignment disc being in fluid communication with the vent port and the pressure port, respectively, of the second end plate; and
   a movable sealing cap disposed in an opening in the first plate and movable along the central axis of the bore.

2. The apparatus of claim 1 wherein the first and second open ends of the main body include pilot diameters that mate with recesses formed in the first and second end plates, respectively.

3. The apparatus of claim 1 further comprising seals disposed between the first and second end plates and the first and second open ends of the main body, respectively.

4. The apparatus of claim 1 further comprising a hollow component having an open base and an open top, the open base of the hollow component being inserted over the alignment disc, the movable sealing cap closing the open top of the hollow component.

5. The apparatus of claim 4 further comprising a seal disposed between the open base of the hollow component and the second end plate and a seal disposed between the open top of the hollow component and the movable sealing cap.

6. The apparatus of claim 5 wherein pressure inside the hollow component is greater than atmospheric and wherein the movable sealing cap includes a groove formed in a bottom surface thereof, the seal between the open top of the hollow component and the movable sealing cap being disposed in the groove.

7. The apparatus of claim 5 wherein pressure in a space between the hollow component and the main body is greater than atmospheric, the apparatus further comprising a seal disposed between the movable sealing cap and the opening in the first end plate that contains the movable sealing cap.

8. The apparatus of claim 7 wherein the movable sealing cap includes a groove formed in a bottom surface thereof, the seal between the open top of the hollow component and the movable sealing cap being disposed in the groove.

9. The apparatus of claim 8 wherein the seal between the open top of the hollow component and the movable sealing cap contacts an outermost diameter of the open top of the hollow component.

10. The apparatus of claim 9 wherein the bottom surface of the movable sealing cap includes an inner portion that is substantially perpendicular to the central axis of the main body and an outer portion that is angled with respect to the inner portion, the outer portion including the groove.

11. The apparatus of claim 10 wherein an inner side wall of the groove is angled inward with respect to the central axis and an outer side wall of the groove is angled outward with respect to the central axis.

12. An apparatus for hydrotesting a hollow component having an open base and an open top, comprising:
- a generally cylindrical main body having a bore therethrough that defines first and second open ends, the bore including a central axis, the hollow component being disposed in the bore in the main body;
- first and second end plates fixed to the main body for closing the first and second open ends, the first end plate including a vent port and a pressure port that open into the bore radially outward from the open top of the hollow component, the second end plate including a vent port and a pressure port;
- an alignment disc disposed in the bore and fixed atop the second end plate, the alignment disc including a vent port and a pressure port that open into the bore radially inside the open base of the hollow component, the vent port and the pressure port of the alignment disc being in fluid communication with the vent port and the pressure port, respectively, of the second end plate, the open base of the hollow component being inserted over the alignment disc; and
- a movable sealing cap disposed in an opening in the first plate and movable along the central axis of the bore, the movable sealing cap closing the open top of the hollow component.

13. The apparatus of claim 12 wherein the first and second open ends of the main body include pilot diameters that mate with recessed formed in the first and second end plates, respectively.

14. The apparatus of claim 12 wherein further comprising seals disposed between the first and second end plates and the first and second open ends of the main body, respectively.

15. The apparatus of claim 12 wherein pressure in a space between the hollow component and the main body is greater than atmospheric, the apparatus further comprising a seal disposed between the movable sealing cap and the opening in the first end plate that contains the movable sealing cap.

16. The apparatus of claim 12 further comprising a seal disposed between the open base of the hollow component and the second end plate and a seal disposed between the open top of the hollow component and the movable sealing cap.

17. The apparatus of claim 16 wherein pressure inside the hollow component is greater than atmospheric and wherein the movable sealing cap includes a groove formed in a bottom surface thereof, the seal between the open top of the hollow component and the movable sealing cap being disposed in the groove.

18. The apparatus of claim 16 wherein the movable sealing cap includes a groove formed in a bottom surface thereof, the seal between the open top of the hollow component and the movable sealing cap being disposed in the groove.

19. The apparatus of claim 18 wherein the seal between the open top of the hollow component and the movable sealing cap contacts an outermost diameter of the open top of the hollow component.

20. The apparatus of claim 19 wherein the bottom surface of the movable sealing cap includes an inner portion that is substantially perpendicular to the central axis of the main body and an outer portion that is angled with respect to the inner portion, the outer portion including the groove.

21. The apparatus of claim 20 wherein an inner side wall of the groove is angled inward with respect to the central axis and an outer side wall of the groove is angled outward with respect to the central axis.

* * * * *